United States Patent
Ueno et al.

(10) Patent No.: US 6,451,109 B1
(45) Date of Patent: Sep. 17, 2002

(54) COLUMNAR CRYSTALS OF 6-HYDROXY-2-NAPHTHOIC ACID AND PROCESS FOR MANUFACTURING THE SAME

(75) Inventors: Ryuzo Ueno, Nishinomiya (JP); Masaya Kitayama, Takarazuka (JP); Hiroyuki Kato, Kawanishi (JP); Ryoichi Otsuka, Kobe (JP)

(73) Assignee: Kabushiki Kaisha Ueno Seiyaku Oyo Kenkyujo, Osaka (JP)

( * ) Notice: Subject to any disclaimer, the term of this patent is extended or adjusted under 35 U.S.C. 154(b) by 0 days.

(21) Appl. No.: 09/830,119
(22) PCT Filed: Aug. 18, 2000
(86) PCT No.: PCT/JP00/05535
§ 371 (c)(1), (2), (4) Date: Apr. 24, 2001
(87) PCT Pub. No.: WO01/14307
PCT Pub. Date: Mar. 1, 2001

(30) Foreign Application Priority Data

Aug. 24, 1999 (JP) .......................... 11-236951

(51) Int. Cl.$^7$ .................. C30B 7/00; C30B 21/02; C30B 28/06
(52) U.S. Cl. .................. 117/68; 117/1; 117/2
(58) Field of Search .................. 117/1, 2, 68

(56) References Cited

U.S. PATENT DOCUMENTS 4,057,576 A * 11/1977 Bachmann et al. ......... 562/467
4,916,257 A * 4/1990 von Plessen et al. ....... 562/467

FOREIGN PATENT DOCUMENTS

EP 325925 8/1989

* cited by examiner

*Primary Examiner*—Felisa Hiteshew
(74) *Attorney, Agent, or Firm*—Sughrue Mion, PLLC

(57) ABSTRACT

A process for manufacturing columnar crystals of 6-hydroxy-2-naphthoic acid comprising the steps of, dissolving crude 6-hydroxy-2-naphthoic acid product in an aqueous solvent, adding crystalline 3-hydroxy-2,7-naphthoic acid or columnar crystals as seed crystals, and cooling the mixture to precipitate the desired crystals. The present invention further provides columnar crystals of 6-hydroxy-2-naphthoic acid which have X-ray diffraction peaks 2θ in 16.8–17.8 and/or 21.3–22.3.

9 Claims, 5 Drawing Sheets

COLUMNAR CRYSTALS OF 6-HYDROXY-2-NAPHTHOIC ACID AND PROCESS FOR MANUFACTURING THE SAME

TECHNICAL FIELD

Present invention relates to columnar crystals of 6-hydroxy-2-naphthoic acid and process for manufacturing the same.

BACKGROUND ART 6-hydroxy-2-naphthoic acid has been employed in manufacturing various industrial products especially dyes, pigments and resins. This compound has usually been manufactured by recrystallizing crude product, which is synthesized by means of the Kolbe-Schmitt reaction, from water or water/alcohol solvent. Thus obtained crystals are in the shape of thin scale with low apparent density, large angle of repose and low fluidity. Therefore, the conventional products have difficulties in handling, especially in transporting, feeding and storing.

DISCLOSURE OF INVENTION

The object of the present invention is to provide a process for manufacturing crystalline product of 6-hydroxy-2-naphthoic acid with high apparent density and good fluidity. Due to the present invention, difficulties in handling, especially in transporting, feeding and storing the product can be reduced.

The present invention provides a process for manufacturing columnar crystals of 6-hydroxy-2-naphthoic acid comprising the steps of; dissolving crude 6-hydroxy-2-naphthoic acid in an aqueous solvent, adding crystalline 3-hydroxy-2,7-naphthoic acid as seed crystals to the solution, and cooling the mixture to precipitate columnar crystals.

In another embodiment, the present invention provides a process for manufacturing columnar crystals of 6-hydroxy-2-naphthoic acid comprising the steps of; dissolving crude 6-hydroxy-2-naphthoic acid in an aqueous solvent, adding columnar crystals of 6-hydroxy-2-naphthoic acid as seed crystals to the solution, and cooling the mixture to precipitate columnar crystals.

By virtue of the present invention, manufacturing columnar crystals of 6-hydroxy-2-naphthoic acid was succeeded for the first time. Accordingly, the present invention also provides columnar crystals of 6-hydroxy-2-naphthoic acid having an X-ray diffraction pattern containing peaks (2θ) in 16.8–17.8 and/or 21.3–22.3.

The columnar crystals of 6-hydroxy-2-naphthoic acid manufactured by the present process exhibit high apparent density and good fluidity, and therefore, the product of the present invention is far easier in handling, especially in storing, transporting and feeding, than conventional thin scale-form crystals.

BEST MODE FOR CARRYING OUT THE INVENTION

Figure 1:
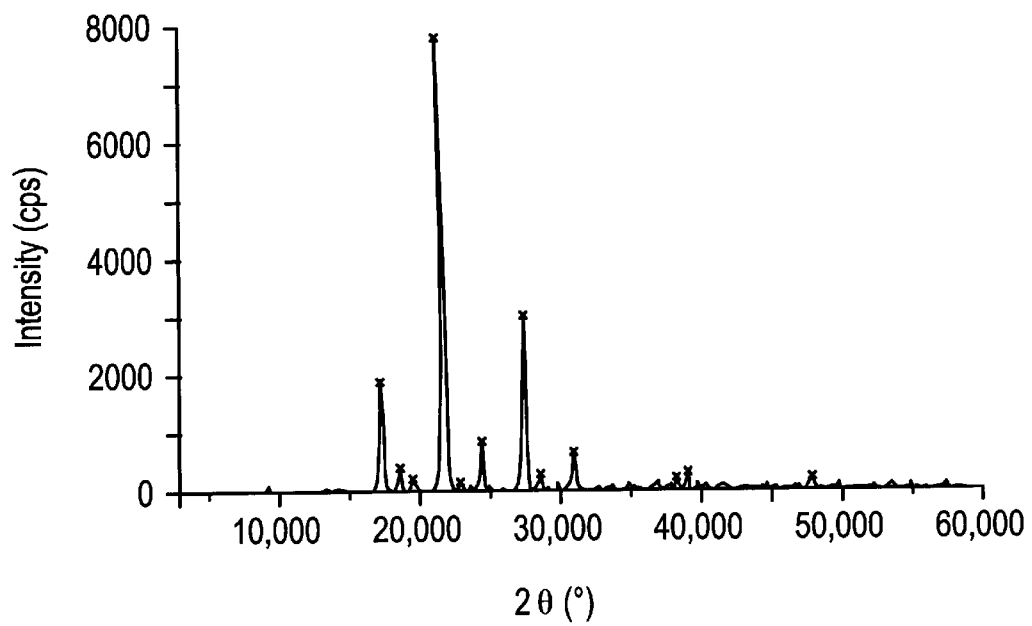
FIG. 1 is a chart of the X-ray diffraction pattern for the purified 6-hydroxy-2-naphthoic acid produced in example 1.

The columnar crystals of 6-hydroxy-2-naphthoic acid of the present invention may be manufactured by recrystallizing crude 6-hydroxy-2-naphthoic acid product synthesized by a conventional manner, for example, by means of the Kolbe-Schmitt method. The starting crude 6-hydroxy-2-naphthoic acid product usually contains more than 80wt % of 6-hydroxy-2-naphthoic acid and also impurities including 3-hydroxy-2,7-naphthoic acid, 2-hydroxy-1-naphthoic acid and unreacted β-naphthol. For the manufacture of dies or pigments, it is preferable to purify 6-hydroxy-2-naphthoic acid product to give the purity of more than 98wt %.

According to the present invention, an aqueous solvent is employed for recrystallizing the crude 6-hydroxy-2-naphthoic acid. The aqueous solvent is not specifically limited and water and water-soluble organic solvents are preferably employed independently or in combination. Examples of the water-soluble organic solvents may include mixed solvent of lower alcohols such as methanol, ethanol and isopropanol. Aqueous alkaline solution, such as potassium hydroxide may also be preferably used.

Preferred aqueous solvents may include a mixture of water and a lower alcohol, especially methanol. The ratio between water and the alcohol in the mixture is not limited. Preferred mixture consists of 100 parts by weight of water and 5–300, more preferably 20–150 parts by weight of alcohol.

When an alkaline aqueous solvent such as aqueous potassium hydroxide is employed, the solvent may be adjusted to contain 0.001–0.2N, preferably to 0.01–0.05N of potassium hydroxide.

The aqueous solvent used in the present invention may contain both of an alkali and a lower alcohol. In addition, the aqueous solvent may further contain dioxane, tetrahydrofuran and the like.

According to the present process, crude 6-hydroxy-2-naphthoic acid is added to the aqueous solvent, and the mixture is heated to an appropriate temperature so that the 6-hydroxy-2-naphthoic acid is dissolved completely. One part by weight of the crude 6-hydroxy-2-naphthoic acid may be dissolved in 1–20, preferably 3–10 parts by weight of the aqueous solvent. The mixture may be heated to a temperature where the 6-hydroxy-2-naphthoic acid is completely dissolved. The temperature may be determined depending on the employed aqueous solvent. For the skilled artisan in this technical field, it will be easy to determine the temperature. For example, when a mixed solvent of water and a lower alcohol is employed, the temperature may vary depending on the type of alcohol and the ratio between the alcohol and water, and typically it may be in the range of 50–180° C.

The aqueous solvent may be heated under pressure. The suitable pressure may vary depending of the kind and mixing ratio of the aqueous solvent. The pressure may preferably be in the range of 0.2–1.0 MPa(gauge pressure).

In the first embodiment of the present invention, seed crystals are added to the aqueous solution of 6-hydroxy-2-naphthoic acid, and then, the desired crystals are obtained by recrystallization. By adding crystalline particles of 3-hydroxy-2,7-naphthoic acid as seed crystals, columnar crystals of 6-hydroxy-2-naphthoic acid can be obtained.

The shape of the 3-hydroxy-2,7-naphthoic acid seed crystal is not specifically limited. The size (diameter) of the seed crystals (considered as spheres) may be less than 1 mm, preferably less than 0.2 mm, and more preferably, less than 0.05 mm.

In the second embodiment of the present invention, columnar crystals of 6-hydroxy-2-naphthoic acid may be employed as seed crystals. The seed crystals in this embodiment can be prepared according to the present invention. The size (diameter) of 6-hydroxy-2-naphthoic acid seed crystals (considered as spheres) may be less than 1 mm, preferably less than 0.2 mm, and more preferably less than 0.05 mm. According to the present invention, the most preferable seed crystals are columnar crystals of 6-hydroxy-2-naphthoic acid.

In any event, 0.1–10 parts by weight, preferably 0.3–3 parts by weight of the seed crystals may be added per 100 parts by weight of crude 6-hydroxy-2-naphthoic acid product to be purified.

The aqueous 6-hydroxy-2-naphthoic acid solution is preferably adjusted to around the saturation temperature, especially, in the range of ±3° C. to the saturation temperature when the seed crystals are added thereto.

After the seed crystals are added, the mixture may be cooled gradually with gently stirring. The mixture may be cooled to a predetermined temperature and kept at the temperature with or without stirring to grow the crystals. The temperature of this aging step is not limited and it is convenience to determine the temperature in the range 20–100° C. based on the temperature of the next filtering step. The time for the aging step may be determined based on the period required for precipitation of the crystals and in general 5–180 minutes.

The precipitated crystals may be washed, filtered nd dried in the conventional manner. For example, thus obtained crystals may be washed with water, filtered with filter cloth by centrifugation, and dried with a hot air dryer.

When a high-purity product is desired, the second embodiment of the present invention, in which the columnar crystals obtained by the present invention are used as seed crystals, may be repeated until desired purity is attained.

The process of the present invention can provide columnar crystals of 6-hydroxy-2-naphthoic acid compared to the conventional thin scale-shape crystals. Said columnar crystals of the present invention exhibit the following characteristics:

Appearance of the crystals: columnar
Representative values of the X-ray diffraction peaks ($2\theta$): 16.8–17.8 and/or 21.3–22.3.
(Representative values of the X-ray diffraction peaks ($2\theta$) of the conventional scale-shape crystals: 14.6–15.6 and/or 26.3–27.3.)
Angle of repose: 33–45° (Conventional scale-shape crystals: about 50°)
Collapse angle: 25–35° (Conventional scale-shape crystals: about 32–45°)
Apparent density: 0.60–0.80 g/cc (average)(Conventional scale-shape crystals: about 0.40– 0.50 g/cc)
Compression rate: 1–23% (Conventional scale-shape crystals: about 40–50%)
Aggregation rate: 63–98% (Conventional scale-shape crystals: about 25–73%)
Spatula angle: 30–55° (average) (Conventional scale-shape crystals: about 60–75°)
Fluidity index: 50–65 (Conventional scale-shape crystals: about 25–35).

The parenthesized numbers represent physical properties of the scale-shape crystals obtained in the conventional manner. Since the X-ray diffraction patterns of the crystals of the present invention significantly differ from those of the conventional scale-shape crystals, it is appeared that the crystallographic structure of the columnar crystals obtained by the present process is substantially altered from that of the conventional product.

As a consequence of being columnar crystals, the obtained product has high apparent density and therefore, requires reduced volume for storing and transporting and exhibits good fluidity. Therefore, common problems associated with the conventionally obtained products, such as hopper congestion and transporting pipe adherence, can be avoided and transportation of the product by conveyance system becomes easier to operate. Consequently, the feeding process of the product becomes easier.

The present invention is further illustrated by means of the attached examples.

EXAMPLE 1

To a 1 L autoclave, 90 g of 6-hydroxy-2-naphthoic acid and 450 g of water were fed and heated to 150° C. (gauge pressure: 0.42 MPa) to give an aqueous solution of 6-hydroxy-2-nphthoic acid. 2.7 g of 3-hydroxy-2,7-naphthoic acid seed crystals (UENO FINE CHEMICALS INDUSTRY, LTD.) having particle size of about 30 μm obtained by the Kolbe-Schmitt method were added to the solution. The mixture was cooled at the rate of 0.5° C./minute to 80° C., and kept at this temperature for 30 minutes to grow the crystals. The obtained crystals were filtered at the same temperature to give 85 g of columnar crystals. The X-ray diffraction pattern of the obtained columnar crystal is shown in FIG. 1. Representative values of X-ray diffraction angle ($2\theta$) are shown in table 1, ingredients in table 2, size distribution in table 3 and various solid state properties in table 4.

X-ray diffraction analysis was carried out under the following conditions:
Device: RINT-1500 (KABUSHIKI KAISHA RIGAKUSHA)
Conditions:
X-ray source: Cu Kα beam
Wave length: 1.54056 Å
Rotation speed: 60 rpm
Scan speed: 4.00° /minute
Ingredient analysis: High speed liquid chromatography
Device: Waters 2690
Detector: Waters 486
Condition: UV wavelength:229 nm
Eluent: $H_2O$ of pH2.3/MeOH=6/4
Flow rate: 1.0 ml/minute

EXAMPLE 2

Figure 2:
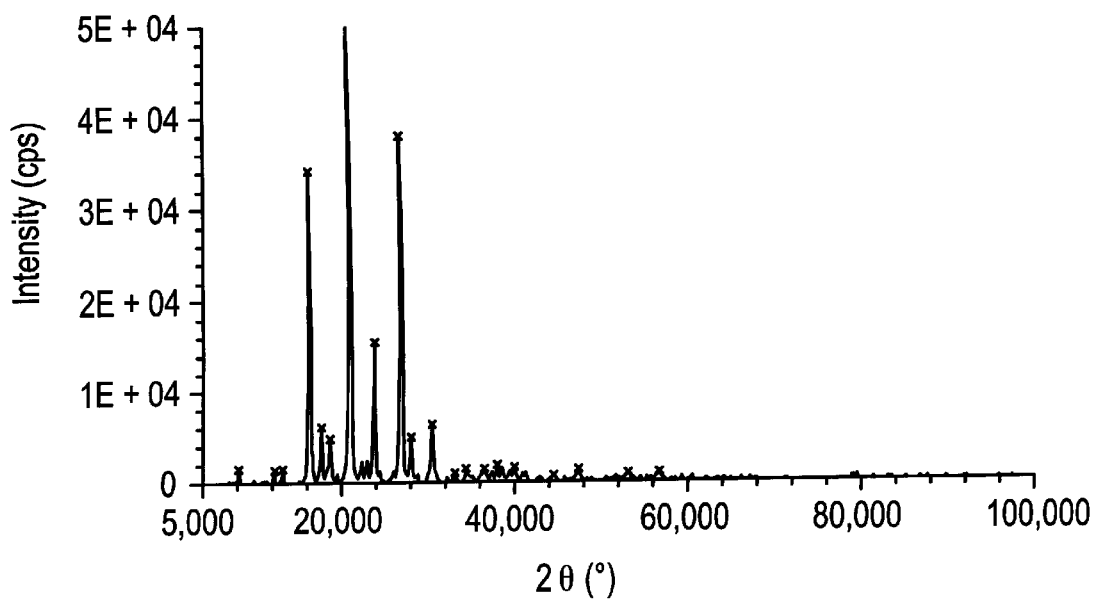
FIG. 2 is a chart of the X-ray diffraction pattern for the purified 6-hydroxy-2-naphthoic acid produced in example 2.

To a 1 L autoclave, 100 g of crude 6-hydroxy-2-naphthoic acid (UENO FINE CHEMICALS INDUSTRY, LTD) obtained by means of the Kolbe-Schmitt method and 650 g of water were fed and the mixture was heated to 150° C. (gauge pressure: 0.42 MPa) to give an aqueous solution of 6-hydroxy-2-nphthoic acid. One gram of the columnar crystals of 6-hydroxy-2-naphthoic acid prepared in Example 1 having particle size of about 100 μm were added to the solution as seed crystals. The mixture was cooled at the rate of 0.5° C./minute to 80° C., and kept at this temperature for 30 minutes to grow the crystals. The obtained crystals were filtered at the same temperature to give 90 g of columnar crystals. The X-ray diffraction pattern of the obtained columnar crystal is shown in FIG. 2. Representative values of X-ray diffraction angle (2θ) are shown in table 1, ingredients in table 2, size distribution in table 3 and various solid state properties in table 4.

The crude 6-hydroxy-2-naphthoic acid product used in the Example was consisted of the following ingredients:

6-hydroxy-2-naphthoic acid >97 wt %
3-hydroxy-2-naphthoic acid 0.61 wt %
3-hydroxy-2,7-naphthoic acid 0.16 wt %
β-naphthol 0.01 wt %

Comparative Example 1

Figure 3:
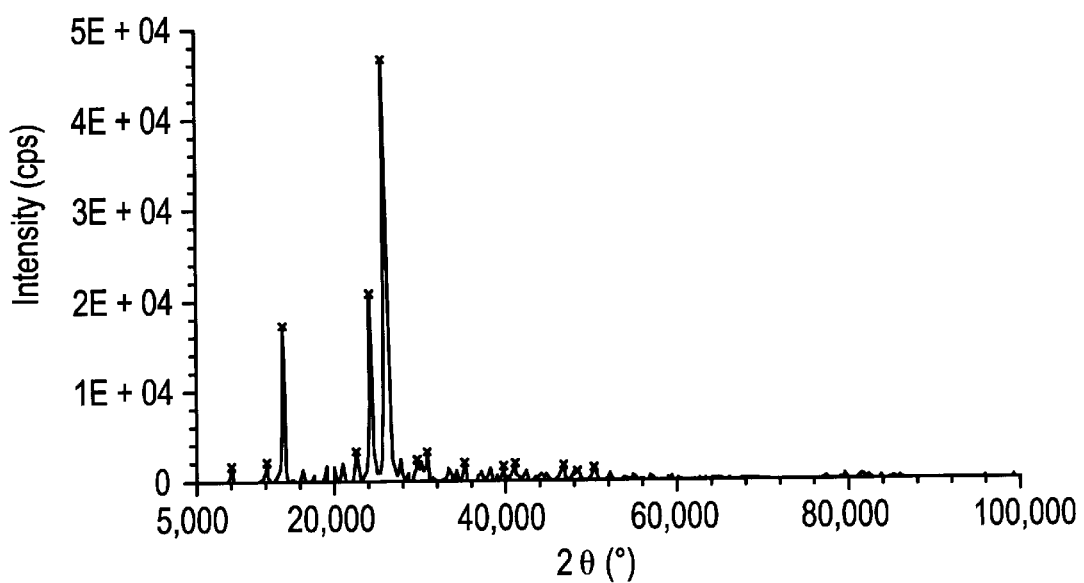
FIG. 3 is a chart of the X-ray diffraction pattern for the purified 6-hydroxy-2-naphthoic acid produced in comparative example 1.

The same crude 6-hydroxy-2-naphthoic acid product as Example 2 was purified in the same manner as Example 2 except that the seed crystals were not added and 90 g of scale-shape crystals were obtained. The X-ray diffraction pattern of the obtained scale-shape crystals is shown in FIG. 3. Representative values of X-ray diffraction angle (2θ) are shown in table 1, ingredients in table 2, size distribution in table 3 and various solid state properties in table 4.

EXAMPLE 3

Figure 4:
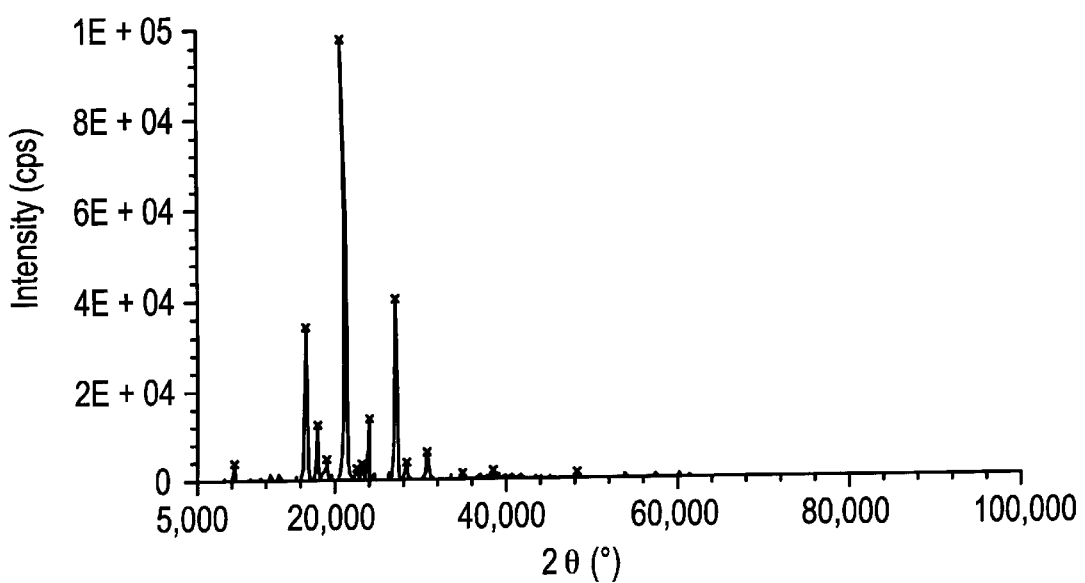
FIG. 4 is a chart of the X-ray diffraction pattern for the purified 6-hydroxy-2-naphthoic acid produced in example 3.

One hundred grams of the scale-shape crystals obtained in Comparative Example 1 were further purified in the same manner as Example 2 to give 90 g of columnar crystals. The X-ray diffraction pattern of the obtained columnar crystals is shown in FIG. 4. Representative values of X-ray diffraction angle (2θ) are shown in table 1, ingredients in table 2, size distribution in table 3 and various solid state properties in table 4.

Comparative Example 2

Figure 5:
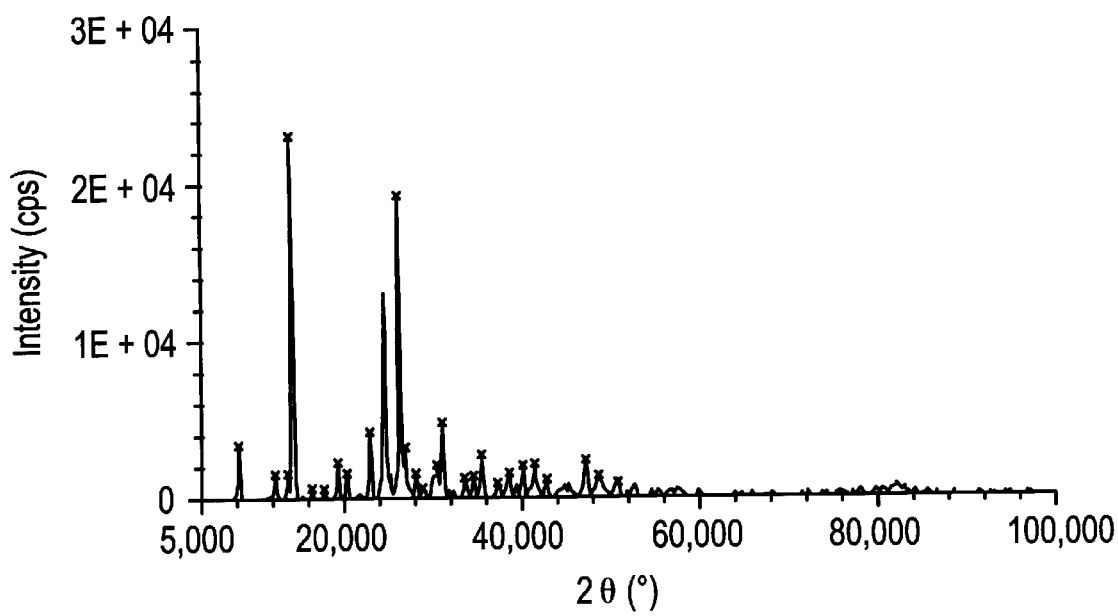
FIG. 5 is a chart of the X-ray diffraction pattern for the purified 6-hydroxy-2-naphthoic acid produced in comparative example 2.

The process of Example 2 was carried out except that 100 g of the scale-shape crystals obtained in Comparative Example 1 were used as starting material and also as seed crystals and 90 g of scale-shape crystals were obtained. The X-ray diffraction pattern of the obtained scale-shape crystals is shown in FIG. 5. Representative values of X-ray diffraction angle (2θ) are shown in table 1, ingredients in table 2, size distribution in table 3 and various solid state properties in table 4.

EXAMPLE 4

Figure 6:
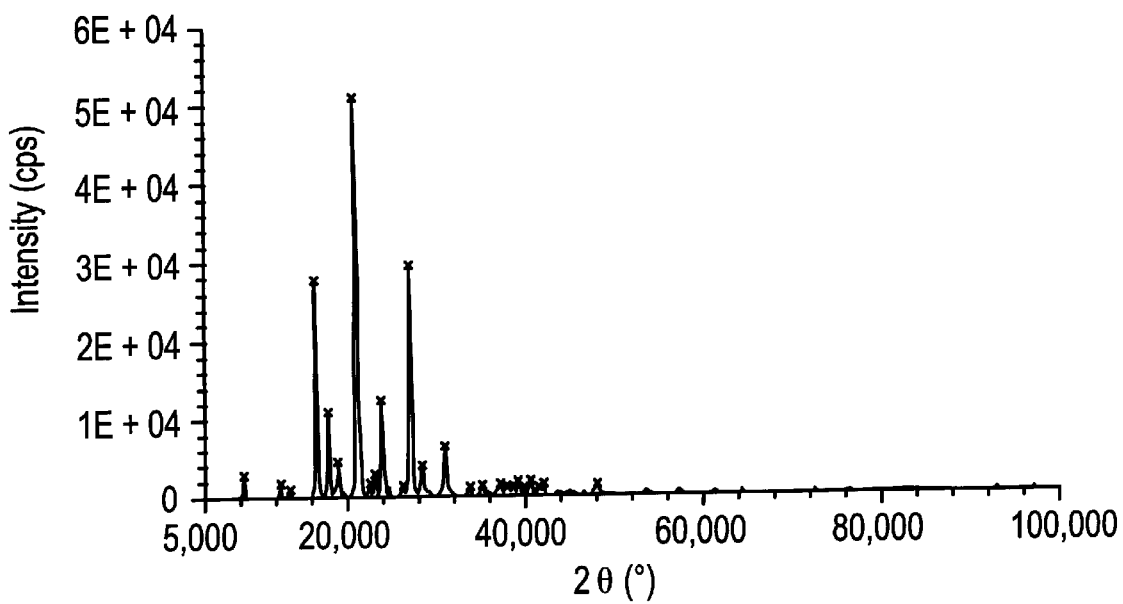
FIG. 6 is a chart of the X-ray diffraction pattern for the purified 6-hydroxy-2-naphthoic acid produced in example 4.

To a 1 L kolben, 100 g of scale-shape crystalline 6-hydroxy-2-naphthoic acid obtained in Comparative Example 1, 325 g of water and 325 g of methanol were fed and heated to 75° C. to give an aqueous solution of 6-hydroxy-2-naphthoic acid. One gram of the columnar crystals of 6-hydroxy-2-naphthoic acid obtained in Example 1 having particle size of about 100 μm were added to the solution as seed crystals. The mixture was cooled at the rate of 0.5° C./minute to 25° C., and kept at this temperature for 30 minutes to grow the crystals. The obtained crystals were filtered at the same temperature to give 90 g of columnar crystals. The X-ray diffraction pattern of the obtained columnar crystal is shown in FIG. 6. Representative values of X-ray diffraction angle (2θ) are shown in table 1, ingredients in table 2, size distribution in table 3 and various solid state properties in table 4.

Comparative Example 3

Figure 7:
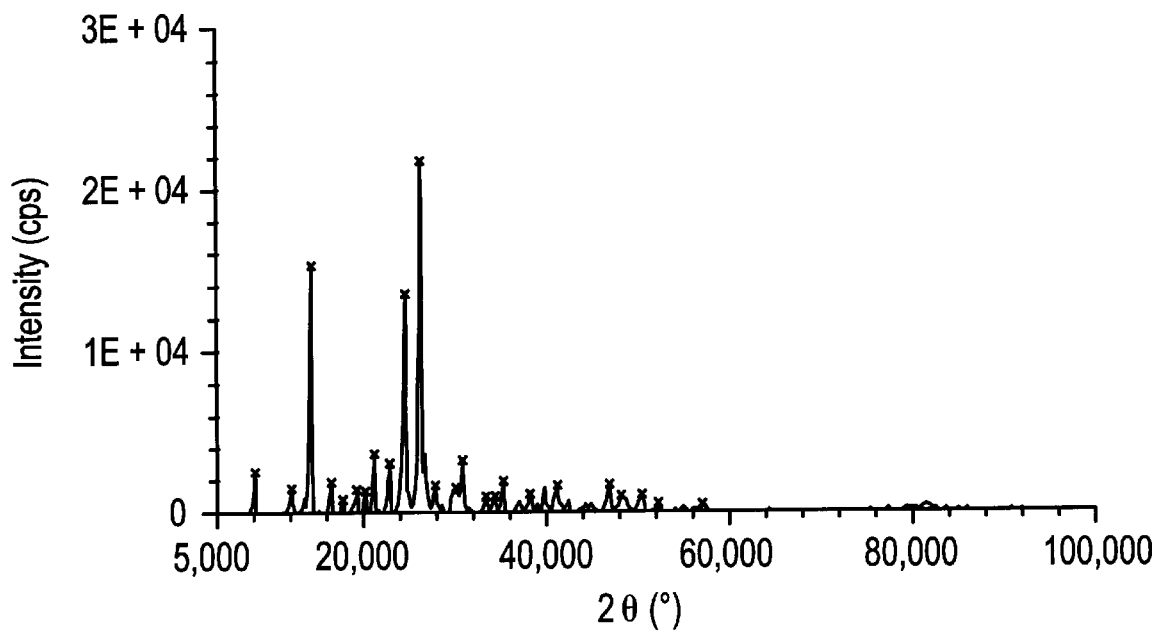
FIG. 7 is a chart of the X-ray diffraction pattern for the purified 6-hydroxy-2-naphthoic acid produced in comparative example 3.

The process of Example 4 was carried out except that the scale-shape crystals obtained in Comparative example 1 were used as seed crystals, and 90 g of scale-shape crystals were obtained. The X-ray diffraction pattern of the obtained scale-shape crystals is shown in FIG. 7. Representative values of X-ray diffraction angle (2θ) are shown in table 1, ingredients in table 2, size distribution in table 3 and various solid state properties in table 4.

Comparative Example 4

Figure 8:
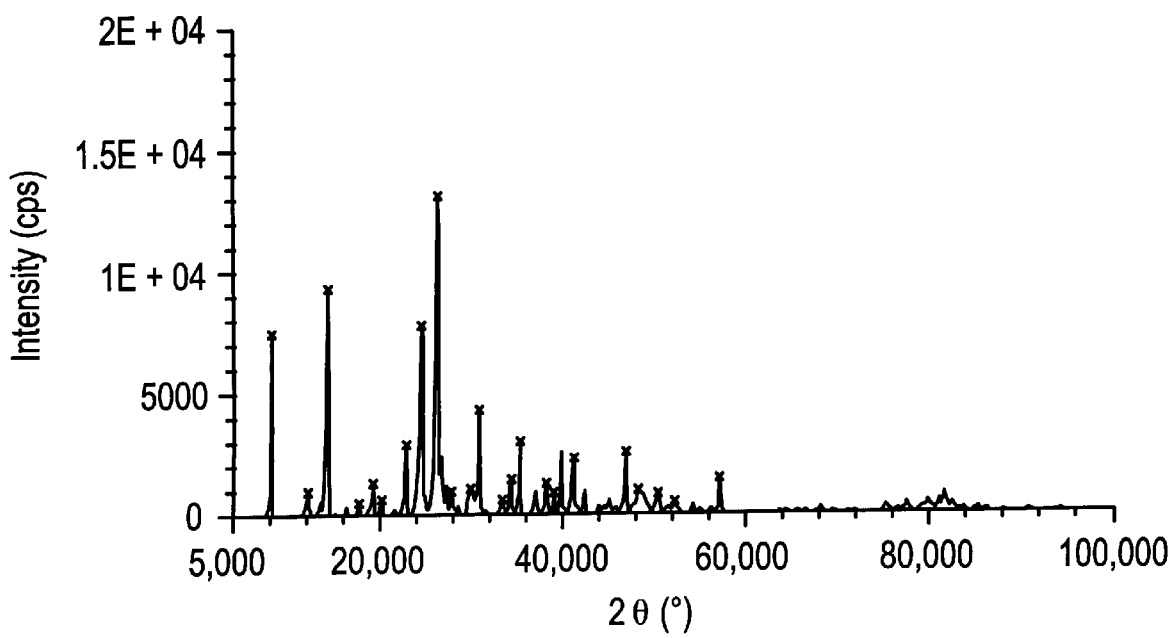
FIG. 8 is a chart of the X-ray diffraction pattern for the purified 6-hydroxy-2-naphthoic acid produced in comparative example 4.

The process of Example 4 was carried out except that no seed crystals were added, and 90 g of scale-shape crystals were obtained. The X-ray diffraction pattern of the obtained scale-shape crystals is shown in FIG. 8. Representative values of X-ray diffraction angle (2θ) are shown in table 1, ingredients in table 2, size distribution in table 3 and various solid state properties in table 4.

EXAMPLE 5

Figure 9:
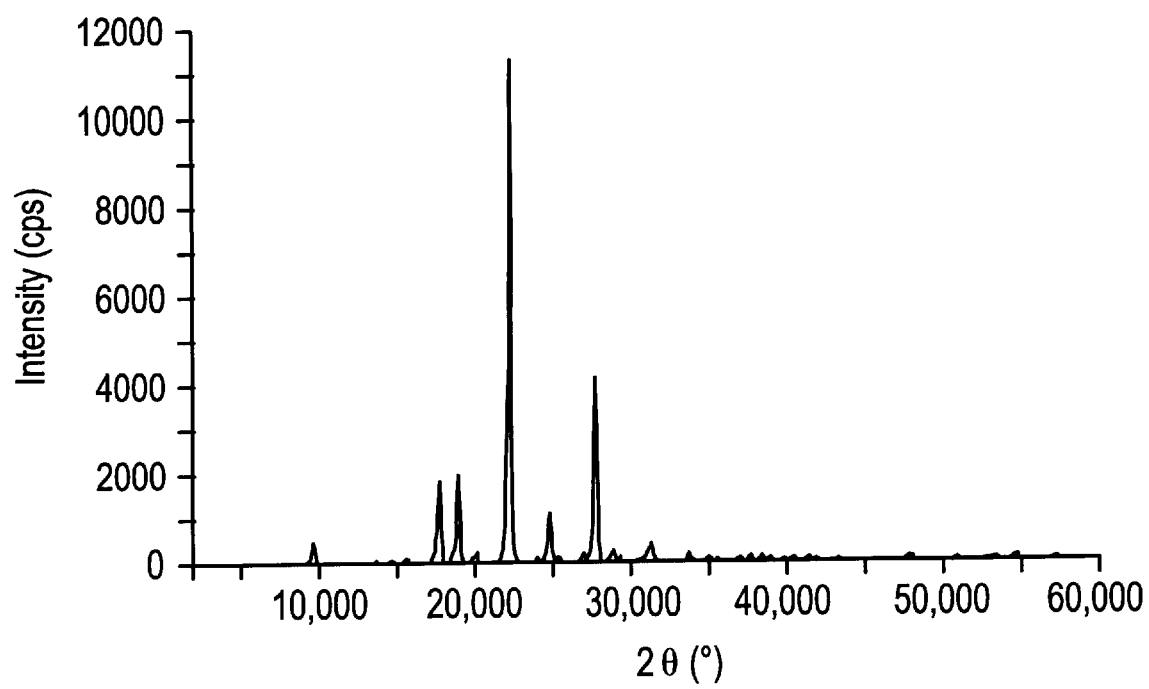
FIG. 9 is a chart of the X-ray diffraction pattern for the purified 6-hydroxy-2-naphthoic acid produced in example 5.

To a 1 L kolben, 200 g of crude 6-hydroxy-2-naphthoic acid (UENO FINE CHEMICALS INDUSTRY, LTD.) obtained by means of Kolbe-Schmitt method, 420 g of water, 180 g of methanol and 1.7 g of 48% aqueous sodium hydroxide were fed and heated to 120° C. under pressure (gauge pressure: 0.28 MPa) to give an aqueous solution of 6-hydroxy-2-naphthoic acid. Two grams of the columnar crystals obtained in Example 1 having particle size of about 100 μm were added to the solution as seed crystals. The mixture was cooled at the rate of 0.5° C./minute to 60° C., and kept at this temperature for 30 minutes to grow the crystals. The obtained crystals were filtered at the same temperature to give 170 g of columnar crystals. The X-ray diffraction pattern of the obtained columnar crystals is shown in FIG. 9. Representative values of X-ray diffraction angle (2θ) are shown in table 1 , ingredients in table 2, size distribution in table 3 and various solid state properties in table 4.

TABLE 1

| | Ex. 1 | Ex. 2 | Comp. Ex. 1 | Ex. 3 | Comp. Ex. 2 | Ex. 4 | Comp. Ex. 3 | Comp. Ex. 4 | Ex. 5 |
|---|---|---|---|---|---|---|---|---|---|
| Representative X-ray diffraction angle | 17.37 21.94 | 17.32 21.88 | 15.14 25.18 | 17.28 21.84 | 15.14 25.14 | 17.28 21.82 | 15.20 25.22 | 15.10 25.12 | 17.56 22.11 |

TABLE 2

| Ingredients (wt %) | Example 1 | Example 2 | Comp. example 1 | Example 3 | Comp. example 2 | Example 4 | Comp. example 3 | Comp. example 4 | Example 5 |
|---|---|---|---|---|---|---|---|---|---|
| 6-hydroxy-2-naphthoic acid | >99.0 | >99.0 | >99.0 | >99.0 | >99.0 | >99.0 | >99.0 | >99.0 | >99.0 |
| 3-hydroxy-2-naphthoic acid | 0.04 | 0.11 | 0.17 | 0.04 | 0.04 | 0.02 | 0.02 | 0.03 | 0.04 |
| 3-hydroxy-2,7-naphthoic acid | 0.44 | 0.03 | 0.12 | 0.03 | 0.10 | 0.02 | 0.04 | 0.10 | 0.03 |
| 2-hydroxy-1-naphthoic acid | 0.03 | 0.03 | 0.04 | 0.03 | 0.04 | 0.02 | 0.04 | 0.10 | 0.00 |
| β-naphthol | 0.00 | 0.00 | 0.00 | 0.00 | 0.00 | 0.00 | 0.00 | 0.00 | 0.00 |

TABLE 3

| Particle size (μm) | Example 1 (wt %) | Example 2 (wt %) | Comp. example 1 (wt %) | Example 3 (wt %) | Comp. example 2 (wt %) | Example 4 (wt %) | Comp. example 3 (wt %) | Comp. example 4 (wt %) | Example 5 (wt %) |
|---|---|---|---|---|---|---|---|---|---|
| ~840 | 6.74 | 1.79 | 1.93 | 1.49 | 1.44 | 2.29 | 0.77 | 2.29 | 8.98 |
| 840~300 | 76.59 | 84.83 | 12.26 | 91.65 | 6.81 | 26.57 | 3.57 | 2.87 | 47.09 |
| 300~180 | 11.61 | 6.41 | 27.99 | 1.59 | 28.19 | 32.93 | 25.46 | 8.22 | 16.81 |
| 180~105 | 3.87 | 3.30 | 35.13 | 4.17 | 32.79 | 18.21 | 23.63 | 22.09 | 14.52 |
| 105~75 | 0.00 | 1.70 | 12.16 | 0.70 | 15.24 | 7.76 | 10.22 | 22.56 | 6.02 |
| 75~45 | 0.99 | 1.41 | 7.92 | 0.40 | 10.74 | 9.35 | 20.92 | 30.98 | 5.06 |
| 45~ | 0.20 | 0.56 | 2.61 | 0.00 | 4.79 | 2.89 | 15.43 | 10.99 | 1.53 |
| Total | 100.0 | 100.0 | 100.0 | 100.0 | 100.0 | 100.0 | 100.0 | 100.0 | 100.0 |

TABLE 4

| | angle of repose (deg.) | collapse angle (deg.) | difference angle (deg.) | apparent density (g/cc) | | | compression rate (%) | aggregation rate (%) | spatula angle (deg.) | | | dispersion rate (%) | fluidity index |
|---|---|---|---|---|---|---|---|---|---|---|---|---|---|
| | | | | aerated | packed | average | | | A1 | A2 | average | | |
| Example 1 | 35.3 | 26.7 | 8.6 | 0.676 | 0.694 | 0.685 | 2.5 | 97.7 | 52.7 | 43.2 | 47.9 | 12.6 | 61.0 |
| Example 2 | 33.9 | 27.3 | 6.6 | 0.615 | 0.628 | 0.622 | 2.0 | 97.6 | 64.3 | 44.7 | 54.5 | 15.4 | 62.0 |
| Comp. Ex. 1 | 52.9 | 32.7 | 20.2 | 0.290 | 0.532 | 0.411 | 45.4 | 61.3 | 64.4 | 61.6 | 63.0 | 10.1 | 28.0 |
| Example 3 | 39.3 | 31.1 | 8.2 | 0.673 | 0.680 | 0.677 | 1.0 | 97.8 | 52.9 | 45.0 | 48.9 | 15.9 | 59.0 |
| Comp. Ex. 2 | 49.1 | 33.6 | 15.5 | 0.300 | 0.564 | 0.432 | 46.8 | 73.0 | 73.9 | 68.6 | 71.2 | 4.9 | 26.0 |
| Example 4 | 44.1 | 28.3 | 15.8 | 0.555 | 0.717 | 0.636 | 22.5 | 79.0 | 55.8 | 47.4 | 51.5 | 5.6 | 50.0 |
| Comp. Ex. 3 | 46.4 | 34.5 | 11.9 | 0.334 | 0.597 | 0.466 | 44.0 | 70.4 | 74.7 | 69.3 | 72.0 | 4.3 | 30.5 |
| Comp. Ex. 4 | 48.0 | 34.7 | 13.3 | 0.163 | 0.513 | 0.388 | 48.7 | 26.9 | 69.5 | 66.6 | 68.0 | 11.7 | 36.0 |
| Example 5 | 42.3 | 32.1 | 10.2 | 0.688 | 0.729 | 0.684 | 12.5 | 76.8 | 55.1 | 47.9 | 51.5 | 5.8 | 55 |

EXAMPLE 6

To a 1 L autoclave, 100 g of the same crude 6-hydroxy-2-naphthoic acid (UENO FINE CHEMICALS INDUSTRY, LTD) as used in Example 2, 500 g of water and 0.5 g of potassium hydroxide were fed and heated to 150° C.(gauge pressure: 0.42 MPa) to give aqueous solution of 6-hydroxy-2-naphthoic acid. One gram of the columnar crystals obtained in Example 1 having particle size of about 100 μm were added to the mixture as seed crystals. The mixture was cooled at the rate of 0.5/minute to 80° C. and kept at this temperature for 30 minutes to grow the crystals. The obtained crystals were filtered at the same temperature to give 90 g of columnar crystals. Ingredients and representative values of X-ray diffraction angle (2θ) of the product are shown in table 5, size distribution of the product in table 6 and various solid state properties in table 8.

Comparative Example 5

The process of Example 6 was carried out except that no seed crystals were added, and 90 g of scale-shape crystals were obtained. Ingredients and representative values of X-ray diffraction angle (2θ) of the product are shown in table 5, size distribution in table 6 and various solid state properties in table 8.

TABLE 5

| | | Example 6 | Comp. example 5 |
|---|---|---|---|
| ingredients (wt. %) | 6-hydroxy-2-naphthoic acid | >99.7 | 99.7 |
| | 3-hydroxy-2-naphthoic acid | 0.03 | 0.13 |
| | 3-hydroxy-2.7-naphthoic acid | 0.06 | 0.06 |
| | 2-hydroxy-1-naphthoic acid | 0.03 | 0.05 |
| | β-naphthol | 0.00 | 0.00 |
| Representative X-ray diffraction angle (2θ) | | 17.32 | 15.18 |
| | | 21.88 | 26.86 |

TABLE 6

| Particle size (μm) | Example 6 wt % | Comp. example 5 wt. % |
|---|---|---|
| ~840 | 0.27 | 0.11 |
| 840~300 | 69.56 | 49.14 |
| 300~180 | 5.67 | 29.33 |

TABLE 6-continued

| Particle size(μm) | Example 6 wt % | Comp. example 5 wt. % |
|---|---|---|
| 180~105 | 16.55 | 17.94 |
| 105~75 | 6.08 | 3.29 |
| 75~45 | 1.80 | 0.18 |
| 45~ | 0.06 | 0.00 |
| Total | 100.00 | 100.00 |

EXAMPLE 7

The columnar crystals obtained in Example 6 were sieved to give 12 g of size-controlled product having the size distribution property shown in table 7. The solid state properties of this product were evaluated as of Example 6 and are shown in table 8.

TABLE 7

| Particle size (μm) | Example 7 wt. % | Comp. example 6 wt. % |
|---|---|---|
| ~840 | 0.00 | 0.00 |
| 840~300 | 7.55 | 6.95 |
| 300~180 | 36.54 | 37.15 |
| 180~105 | 40.72 | 42.09 |
| 105~75 | 14.19 | 12.70 |
| 75~45 | 1.01 | 1.11 |
| 45~ | 0.00 | 0.00 |
| Total | 100.00 | 100.00 |

The solid state properties of the obtained crystalline particles were evaluated as follows:

Device: Powdertester Type PT-N (HOSOKAWA MICRON CO., Ltd)

Apparent Density

Aerated apparent density measured before tapping

Packed apparent density measured after tapping

Spatula angle:
  A1=before vibrating
  A2=after vibrating

Fluidity index: determined in the manner described in Chemical Engineering, Jan. 18 (1965) pp-166–167. Fluidity index is a numerical value representing the fluidity of the product. Higher number of fluidity index means higher fluidity.

Comparative Example 7

Twenty grams of 6-hydroxy-2-naphthoic acid obtained by means of Kolbe-Schmitt method was added to a mixed solvent consisting of 160 g of water and 120 g of 1,4-dioxane and heated to give a solution. The solution was cooled and the precipitates were collected by filtration. The precipitates were washed with 30% aqueous dioxane and dried under vacuum to give crystals. X-ray diffraction pattern of thus obtained crystals contained similar peaks as of the scale-shape crystals. The starting material and ingredient of the product are shown in the table 9.

TABLE 9

| | starting material | purified |
|---|---|---|
| 6-hydroxy-2-naphthoic acid | >97.0 | >99.0 |
| 3-hydroxy-2-naphthoic acid | 0.83 | 0.07 |
| 3-hydroxy-2,7-naphthoic acid | 0.26 | 0.04 |
| 2-hydroxy-1-naphthoic acid | 0.05 | 0.04 |
| β-naphthol | 0.02 | 0.00 |

Industrial Applicability

Columnar crystals of 6-hydroxy-2-naphthoic acid product, which is useful in manufacturing various industrial products especially dyes, pigments and resins, can be produced by the process of the present invention. The columnar crystals of 6-hydroxy-2-naphthoic acid of the present invention have high apparent density and exhibit good fluidity, and therefore, can remedy the conventional problems of difficulties in handling, especially in transporting, feeding and storing the product.

What is claimed is:

1. Columnar crystals of 6-hydroxy-2-naphthoic acid which have X-ray diffraction peaks (2θ) in 16.8–17.8 and/or 21.3–22.3.

2. A process for manufacturing columnar crystals of 6-hydroxy-2-naphthoic acid comprising the steps of;
   dissolving crude 6-hydroxy-2-naphthoic acid product in an aqueous solvent,
   adding 3-hydroxy-2,7-naphthoic acid seed crystals to the solution and
   cooling the mixture to precipitate crystals.

3. The process of claim 2, wherein said aqueous solvent is a mixed solvent of water and a lower alcohol.

4. The process of claim 2, wherein said aqueous solvent is water.

5. The process of claim 2, wherein said aqueous solvent is an alkaline aqueous solvent.

TABLE 8

| | angle of repose (deg.) | collapse angle (deg.) | difference angle (deg.) | apparent density (g/cc) | | | compression rate (%) | aggregation rate (%) | spatula angle (deg.) | | | dispersion rate (%) | fluidity index |
|---|---|---|---|---|---|---|---|---|---|---|---|---|---|
| | | | | aerated | packed | average | | | A1 | A2 | average | | |
| Example 6 | 38.8 | 31.8 | 7.0 | 0.749 | 0.796 | 0.773 | 5.9 | 76.3 | 40.7 | 32.4 | 36.6 | 5.4 | 64.0 |
| Comp. Ex. 5 | 51.5 | 45.1 | 6.4 | 0.339 | 0.598 | 0.469 | 43.3 | 54.3 | 73.3 | 63.3 | 68.3 | 6.8 | 33.0 |
| Example 7 | 37.4 | 30.7 | 6.7 | 0.675 | 0.861 | 0.768 | 21.6 | 63.7 | 45.8 | 32.8 | 39.3 | 15.8 | 55.5 |
| Comp. Ex. 6 | 51.7 | 39.0 | 12.7 | 0.318 | 0.623 | 0.470 | 48.9 | 72.3 | 67.3 | 61.4 | 64.3 | 3.4 | 26.0 |

6. A process for manufacturing columnar crystals of 6-hydroxy-2-naphthoic acid comprising the steps of;
dissolving crude 6-hydroxy-2-naphthoic acid product in an aqueous solvent,
adding columnar crystals of 6-hydroxy-2-naphthoic acid as seed crystals to the solution, and
cooling the mixture to precipitate crystals.

7. The process of claim 6, whereing said aqueous solvent is a mixed solvent of water and a lower alcohol.

8. The process of claim 6, wherein said aqueous solvent is water.

9. The process of claim 6, wherein said aqueous solvent is an alkaline aqueous solvent.

* * * * *